US012622761B2

(12) United States Patent
Kwok et al.

(10) Patent No.: US 12,622,761 B2
(45) Date of Patent: May 12, 2026

(54) FLUID-DRIVEN ROBOTIC NEEDLE POSITIONER FOR IMAGE-GUIDED PERCUTANEOUS INTERVENTIONS

(71) Applicant: THE UNIVERSITY OF HONG KONG, Hong Kong (HK)

(72) Inventors: Ka Wai Kwok, Hong Kong (HK); Zhuoliang He, Hong Kong (HK); Ziyang Dong, Hong Kong (HK); Justin Di-Lang Ho, Hong Kong (HK); Ge Fang, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 244 days.

(21) Appl. No.: 18/017,090

(22) PCT Filed: Jul. 20, 2021

(86) PCT No.: PCT/CN2021/107372
§ 371 (c)(1),
(2) Date: Jan. 20, 2023

(87) PCT Pub. No.: WO2022/017384
PCT Pub. Date: Jan. 27, 2022

(65) Prior Publication Data
US 2023/0293253 A1 Sep. 21, 2023

Related U.S. Application Data

(60) Provisional application No. 63/053,798, filed on Jul. 20, 2020.

(51) Int. Cl.
*A61B 90/00* (2016.01)
*A61B 34/37* (2016.01)
*A61B 90/11* (2016.01)

(52) U.S. Cl.
CPC .............. *A61B 34/37* (2016.02); *A61B 90/11* (2016.02); *A61B 90/37* (2016.02)

(58) Field of Classification Search
CPC ......... A61B 34/37; A61B 90/11; A61B 90/37; A61B 2017/00539; A61B 2090/3925;
(Continued)

(56) References Cited

U.S. PATENT DOCUMENTS

| | | | |
|---|---|---|---|
| 6,921,406 B1 * | 7/2005 | Chakeres | A61B 90/11 606/130 |
| 11,998,282 B2 * | 6/2024 | Azizian | A61B 90/96 |

(Continued)

FOREIGN PATENT DOCUMENTS

| | | | | |
|---|---|---|---|---|
| CN | 103200877 A | * | 7/2013 | A61B 34/30 |
| CN | 112804959 A | * | 5/2021 | A61B 1/3132 |

(Continued)

OTHER PUBLICATIONS

G. H. Kim et al., "Shoulder-mounted Robot for MRI-Guided Arthrography: Clinically Optimized System," 2019 41st Annual International Conference of the IEEE Engineering in Medicine and Biology Society (EMBC), Berlin, Germany, 2019, pp. 1977-1980 (Year: 2019).*

(Continued)

*Primary Examiner* — Ramon A. Mercado
*Assistant Examiner* — Shaheda Hoque
(74) *Attorney, Agent, or Firm* — Amin, Turocy & Watson, LLP

(57) ABSTRACT

Disclosed are systems and methods for biopsy, drainage, drug administration, electrode implantation and/or tumor ablation employing percutaneous procedures for diagnostic or therapeutic purposes, performed by inserting a needle or probe through the skin of patient towards target anatomy using a patient mounted robot.

20 Claims, 8 Drawing Sheets

(58) Field of Classification Search
CPC .... A61B 2090/3954; A61B 2090/3966; A61B 34/30
See application file for complete search history.

(56) References Cited

U.S. PATENT DOCUMENTS

| | | | | |
|---|---|---|---|---|
| 2012/0265051 A1* | 10/2012 | Fischer | ................. | A61B 34/37 73/800 |
| 2014/0039298 A1* | 2/2014 | Whitcomb | ............. | A61B 5/064 600/414 |
| 2015/0100066 A1* | 4/2015 | Kostrzewski | ...... | A61B 17/1615 606/130 |
| 2016/0074063 A1* | 3/2016 | Arimitsu | ............ | A61B 10/0233 600/417 |
| 2016/0106508 A1* | 4/2016 | Lathrop | ................. | A61B 90/14 606/130 |
| 2017/0035525 A1* | 2/2017 | Baumgartner | ......... | A61B 90/11 |
| 2017/0181755 A1* | 6/2017 | Librot | .................... | A61B 34/37 |
| 2018/0008358 A1* | 1/2018 | Kostrzewski | .......... | A61B 90/11 |
| 2019/0000575 A1* | 1/2019 | Noonan | ................. | A61B 18/02 |
| 2020/0015910 A1* | 1/2020 | Azizian | .................. | A61B 34/20 |
| 2020/0297451 A1* | 9/2020 | Cameron | ............... | A61B 90/14 |
| 2020/0345524 A1* | 11/2020 | Collins | .................... | A61F 2/95 |
| 2021/0015558 A1* | 1/2021 | Guo | ........................ | A61B 34/37 |
| 2021/0093304 A1* | 4/2021 | Fischer | ............. | A61B 10/0241 |
| 2022/0000565 A1* | 1/2022 | Gururaj | .................. | A61B 17/34 |

FOREIGN PATENT DOCUMENTS

| | | | | | |
|---|---|---|---|---|---|
| EP | 3360502 A2 | * | 8/2018 | ............. | A61B 46/10 |
| FR | 3073135 B1 | * | 11/2019 | ............. | A61B 34/20 |
| JP | 7323489 B2 | * | 8/2023 | ............. | A61B 34/37 |
| WO | WO-03007854 A1 | * | 1/2003 | ........... | A61F 2/4601 |
| WO | WO-2015052719 A1 | * | 4/2015 | ............. | A61B 34/30 |
| WO | WO-2018084869 A1 | * | 5/2018 | ............. | A61B 90/14 |
| WO | WO-2018112424 A1 | * | 6/2018 | ......... | A61B 17/3403 |
| WO | WO-2019207322 A1 | * | 10/2019 | ....... | A61B 17/00234 |

OTHER PUBLICATIONS

K.-H. Lee et al., "MR Safe Robotic Manipulator for MRI-Guided Intracardiac Catheterization," in IEEE/ASME Transactions on Mechatronics, vol. 23, No. 2, pp. 586-595, Apr. 2018 (Year: 2018).*

N. A. Patel, J. Yan, D. Levi, R. Monfaredi, K. Cleary and I. Iordachita, "Body-Mounted Robot for Image-Guided Percutaneous Interventions: Mechanical Design and Preliminary Accuracy Evaluation," 2018 IEEE/RSJ International Conference on Intelligent Robots and Systems (IROS), Madrid, Spain, pp. 144 (Year: 2018).*

Western C, Hristov D, Schlosser J. Ultrasound Imaging in Radiation Therapy: From Interfractional to Intrafractional Guidance. Cureus. Jun. 20, 2015 (Year: 2015).*

A. Bekku, J. Kim, Y. Nakajima and K. Yonenobu, "A body-mounted surgical assistance robot for minimally invasive spinal puncture surgery," 5th IEEE Ras/Embs International Conference on Biomedical Robotics and Biomechatronics, Sao Paulo, Brazil, 2014, pp. 19-23 (Year: 2014).*

X. Xiao et al., "Portable Body-Attached Positioning Mechanism Toward Robotic Needle Intervention," in IEEE/ASME Transactions on Mechatronics, vol. 25, No. 2, pp. 1105-1116, Apr. 2020 (Year: 2020).*

International Search Report, Written Opinion and International Preliminary Report for International Application No. PCT/CN2021/107372 mailed on Oct. 19, 2021, 10 pages.

* cited by examiner

FLUID-DRIVEN ROBOTIC NEEDLE POSITIONER FOR IMAGE-GUIDED PERCUTANEOUS INTERVENTIONS

CROSS REFERENCE TO RELATED APPLICATIONS

This application claims the benefit of the filing dates of U.S. Provisional Application No. 63/053,798, filed on Jul. 20, 2020, the entire contents of which are incorporated by reference herein.

TECHNICAL FIELD

Disclosed are systems and methods for biopsy, drainage, drug administration and/or tumor ablation employing percutaneous procedures for diagnostic or therapeutic purposes, typically performed by inserting a needle or probe through the skin of patient towards target anatomy.

BACKGROUND

Percutaneous procedures are undertaken for diagnostic or therapeutic purposes, typically performed by inserting a needle or probe through the skin of patient towards target anatomy. Applications range from biopsy, drainage, drug administration to tumor ablation, and are applicable to numerous parts of the body including breast and kidneys, with prominence in ablation for liver cancer.

As the sixth most common type of cancer, liver cancer is also one of the primary sources of cancer-related death globally. Hepatocellular carcinoma (HCC) is the most common form of primary liver cancer, with the first-line treatments by liver transplantation and resection for <20% cases. For the remaining unresectable cases, percutaneous radiofrequency (RF) ablation is considered as the standard local ablative therapy (FIG. 1a). During the procedure, an ablation needle (0D=Ø1.2-2.1 mm) is inserted through the skin into the target lesion, typically guided by ultrasound (US) (FIG. 1b), or computed tomography (CT). Multiple needle insertions may be required for completing ablation of large (>Ø3 cm) or multiple tumors. After the ablation, the completeness is typically assessed by post-operative computed tomography (CT) or sonography. Residual tumors will be treated with further ablation or adjunct therapy. However, the procedure has difficulties in treating tumors abutting vessels or organs due to inaccurate ablation margins (<1 cm), which can result in high tumor recurrence (70% at 5 years) or inadvertent organ damage.

To tackle these difficulties, numerous research groups in the past have developed needle guiding devices that improve targeting accuracy and precision by either providing physical guidance for manual insertion or enabling completely automated intervention with a robotic system. Magnetic resonance image (MRI), X-ray/CT, US or a combination of these modalities could be adopted for pre-operative planning, intra-operative (intra-op) feedback/guidance, and post-operative validation. Among them, MRI has been recognized for its advantage of high soft-tissue contrast, and zero ionizing radiation (FIG. 1c). Precise, real-time temperature monitoring (resolution <1° C.) can also be achieved by intra-op MRI to enable monitoring of ablation and its heat diffusion (FIG. 1d). As an alternative to RF ablation, laser ablation provides the opportunity for zero interference with the MRI while simultaneously conducting ablation and MR thermometry. However, the success of MRI-guided ablation still depends on precise intra-tumor probe placement and skin insertion positioning for effective pull-back, both of which require highly experienced operators, and can induce inter-operator variability in ablation results.

In an effort to minimize variability in probe placement, passive needle holders have been developed, such as the commercialized products SeeStar (AprioMed, Uppsala, Sweden) and Simplify (NeoRad AS, Oslo, Norway). Passive devices can assist the manual adjustment of needle orientation and retain a fixed angle for needle insertion. However, intensive manual adjustment by the surgeon is still needed to achieve precise needle placement. This requires the patient to be transferred in and out of the MRI scanner bore to perform adjustment, which will prolong the procedure time.

To this end, MR safe/conditional robot-assist percutaneous systems have been extensively investigated. A CE-marked commercial robotic system Innomotion (Innomedic Inc., Herxheim, Germany) was developed for MRI- and CT-guided needle placement. It is a table-mounted system and features 5-degree-of-freedom (DoF) needle actuation driven by pneumatic cylinders. The system can achieve a mean targeting precision of <0.5 mm, and has been used for MRI-guided percutaneous interventions in 16 patients. Researchers have also developed various prototypes of table/floor-mounted robotic systems for MRI-guided needle procedure, such as the 5-DoF instrument manipulator and the MR compatible needle-guide robot actuated by pneumatic motors. A robot for MRI-guided laser ablation of the liver underwent pilot studies on two patients made use of a gantry to secure the robot over the patients and provided a large workspace (up to 90% of the liver volume) for positioning the insertion point. Other examples include a concentric tube-based needle steering robot for neurosurgical ablation and a leadscrew-based robotic system for breast biopsy that fits between a breast coil and the wall of the MRI bore and reaches the biopsy site by a 90° channel for a bendable needle. Guided by real-time ultrasound imaging, a compact robotic needle manipulator was developed for central venous catheterization (CVC). It has 3-DOF for orientation, positioning of the needle and linear actuation for insertion along with the integrated US probe. An RCM mechanism enables orientation adjustment while the ball screw mechanism enables linear motion. A six-axis force sensor was installed at the contact position of needle to achieve deformation simulation. The detachable design configuration is helpful for sterilization from clinical point of view.

In general, the table/floor-mounted systems can provide a fixed reference frame through the rigid structure, and hence achieve high-accuracy needle targeting. However, the bulky structure of the systems generally occupies a large footprint, which may require a specialized MRI body coil or scanner with larger clearance, as well as alteration of the surgical workflow. Moreover, the potential relative motion between the robot/needle and patient body due to respiration or accidental movement of the patient may pose a safety hazard.

Patient-mounted systems can ensure the safety with respect to the patient movement, as the system and needle can move together with the patient. The Light Puncture Robot (LPR) is a CT— and MRI-compatible system that can achieve needle positioning and insertion by pneumatic pistons. The system could achieve a large needle tip workspace (135 mm×120 mm) above-skin and automatic needle insertion. however, as a result, the overall system footprint is large (368 mm×270 mm×127 mm). A patient-mounted robot (~Ø200 mm) with 4-DoF needle manipulation for MRI-guided arthrography of the pediatric shoulder. A robot for low back pain injections has been developed (219 mm×250 mm×87 mm), consisting of two stacked x-y table mechanisms that could be mounted directly on the patient.

Although many current systems are capable of accurate and automatic needle positioning, they are typically not designed for the simultaneous use of multiple needles, and due to their large footprint, cannot be deployed in multiples to overcome this limitation. For large (>Ø3 cm) and/or multiple tumors, several ablations and insertions are often needed to sufficiently cover the tumor volume. This would prolong the procedure if only one single-needle ablation can be conducted at each time of MRI-guidance. However, few researchers have developed systems in this respect. A patient-mounted imaging-compatible (MRI, CT, X-ray, etc.) robotic positioner small enough to be mounted on an MRI loop coil has been presented. The system was purpose-built for multiple needle insertions, although through a common entry point. This may prevent its application in cases where separate entry points are required. Additionally, in their presented prototype, the remote center of motion (RCM) is located 15 mm above the skin surface due to the system design limited by the motor size. Another example is Robosy, a disposable, patient-mounted robotic platform for percutaneous interventions specifically designed to be operated under CT guidance. Guided by the radiologist in the control room, it remotely grips, orients, and inserts a standard biopsy needle while permitting simultaneous imaging of the needle location. However, multiple adjustments of needle orientation are needed for precise targeting. The targeting accuracy was also limited by the imaging modality especially in applications for brain surgery, as compared to MRI.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

For image-guided percutaneous procedures that require multiple needle insertions, the overall procedure time could be reduced by avoiding the need for rescanning, repositioning, and inserting new needles for each target. To this end, described herein is a small sized patient-mounted robotic system for image-guided percutaneous needle placement, which allows simultaneous needle targeting and insertion at multiple locations with several robots. The key contributions of the systems and methods described herein are listed below:

1) Design of a patient-mounted robotic device for image-guided (MRI, CT, X-ray, etc.) percutaneous procedures. The needle manipulator is semi-automated, with fine adjustment made by the robot after coarse initial placement by the surgeon. Visual feedback is provided to the surgeon during manual operation for clear, interactive operation;

2) The robot is lightweight (189 g) and compact (Ø108 mm×115 mm height), allowing simultaneous needle targeting at multiple locations. Fine adjustment is performed by soft fluid-driven actuators to ensure minimal imaging artifacts under MRI. Granular jamming is adopted for the locking of the needle guide to prevent unwanted movement;

3) Experimental validation of the system is performed, evaluating actuator stiffness, positional targeting error, MR-safety, and needle guide tracking under MRI.

Percutaneous ablation is a standard therapy for most cases of hepatocellular carcinoma (HCC), which is a general type of primary liver cancer. MRI, X-ray/CT, ultra-sound or a combination of these modalities could be adopted as a guidance for intervention procedures of treatments. Among them, MRI offers high-contrast images of soft tissue to monitor the ablation procedure. However, the success of image-guided ablation still depends on precise intra-tumor probe placement and skin insertion positioning, both of which require highly experienced operators, and can induce inter-operator variability in ablation results. In this work, we present a semi-automated robotic system for image-guided percutaneous needle procedures. The compact and light-weight design enables the direct fixture of robot on the patient body and simultaneous needle targeting at multiple locations with several robots. Accurate (0.89±0.31 mm) needle navigation is achieved by incorporating soft fluid-driven actuators with feedback control and stiffness modulation capabilities. The 3D location of the needle guide can be reconfirmed by tracking fiducial markers. The performance of the robotic platform, such as stiffness, needle positioning accuracy and frequency response was experimentally evaluated. Negligible interference to MR imaging was also validated by an MR compatibility test.

Disclosed herein are methods of performing a medical procedure comprising medical imaging to obtain a dataset of a region of interest; identifying a target position on or within a patient and positioning a patient on an operating table; identifying the target position relative to the robot position; determining a needle insertion path, an incision port and robot position based on the data set and the target position; non-invasive mounting of the robot on the patient at the determined incision port and robot position; coarse adjustment of the robot performed manually by a surgeon with visual feedback provided by the robot to indicate adjustment accuracy in-situ; fine adjustment of the robot after coarse adjustment for automatic needle guide positioning guided by intra-operative medical imaging and/or robot encoding.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

Figure 1:
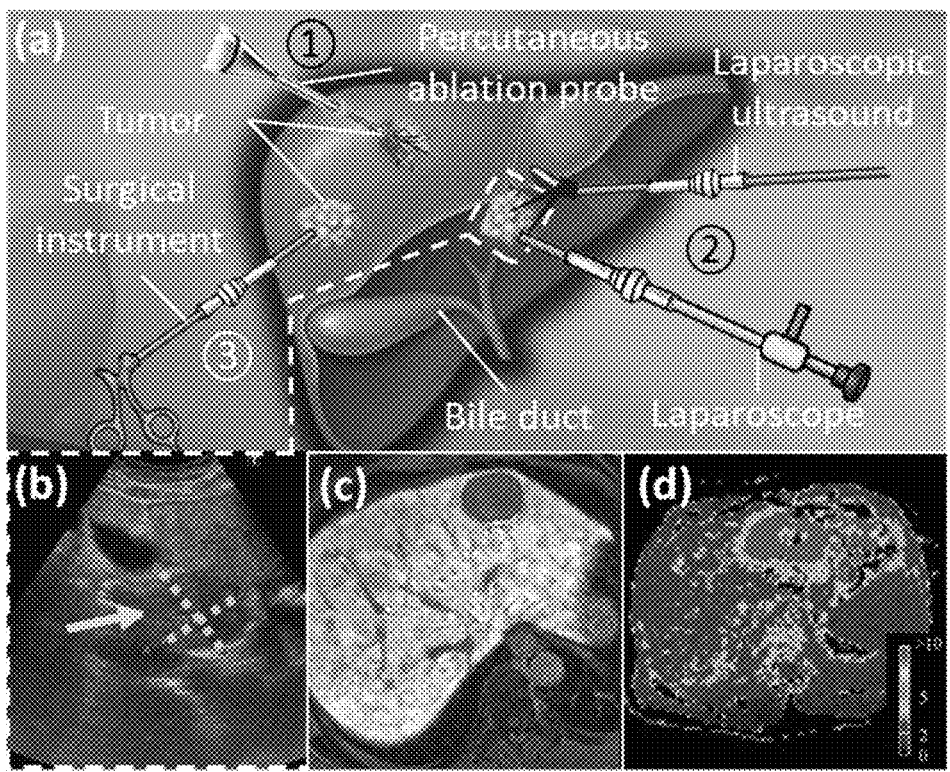
FIG. 1 depicts FIG. 1(a) schematics of the procedures: ① percutaneous RF ablation, ② laparoscopic ablation under abdominal ultrasound, ③ surgical resection; 1(b) Liver tumor of size 5.9×5.7 cm (arrow) in the ultrasound images; 1(c) MR images showing the hepatobiliary carcinoma; 1(d) Thermal MR images during MRI-guided high-intensity focused ultrasound (HIFU).
Figure 2:
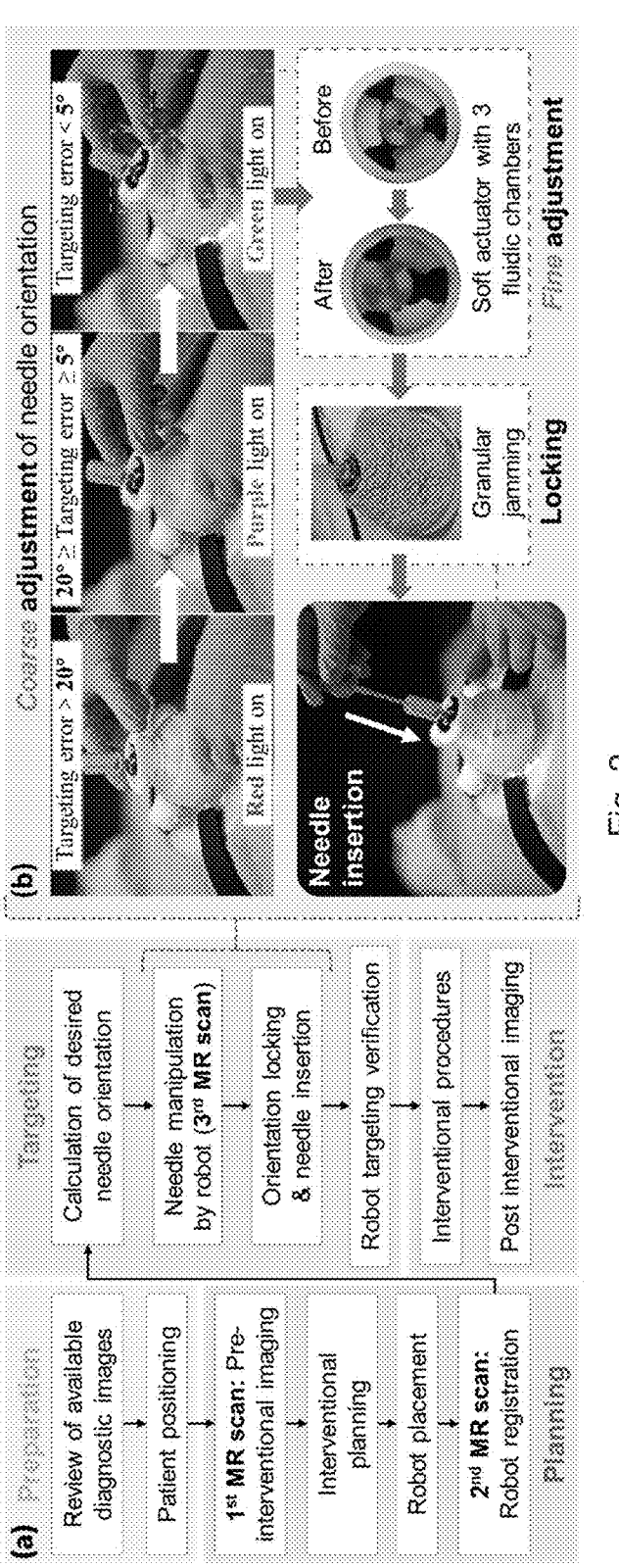
FIG. 2. Depicts in FIG. 2(a) a workflow of MRI-guided percutaneous intervention using the proposed needle robot.

The robotic operation is involved in the targeting stage; and in FIG. 2(b) Coarse adjustment of the needle guide while the patient is out of the scanner bore. Fine adjustment will be tele-operated while being in the bore. The angular error of needle guide is indicated by colored lighting during the coarse adjustment. The warmer the color, larger the error indicated. The needle guide is locked by the operator using granular jamming for a precise needle insertion.

Figure 3:
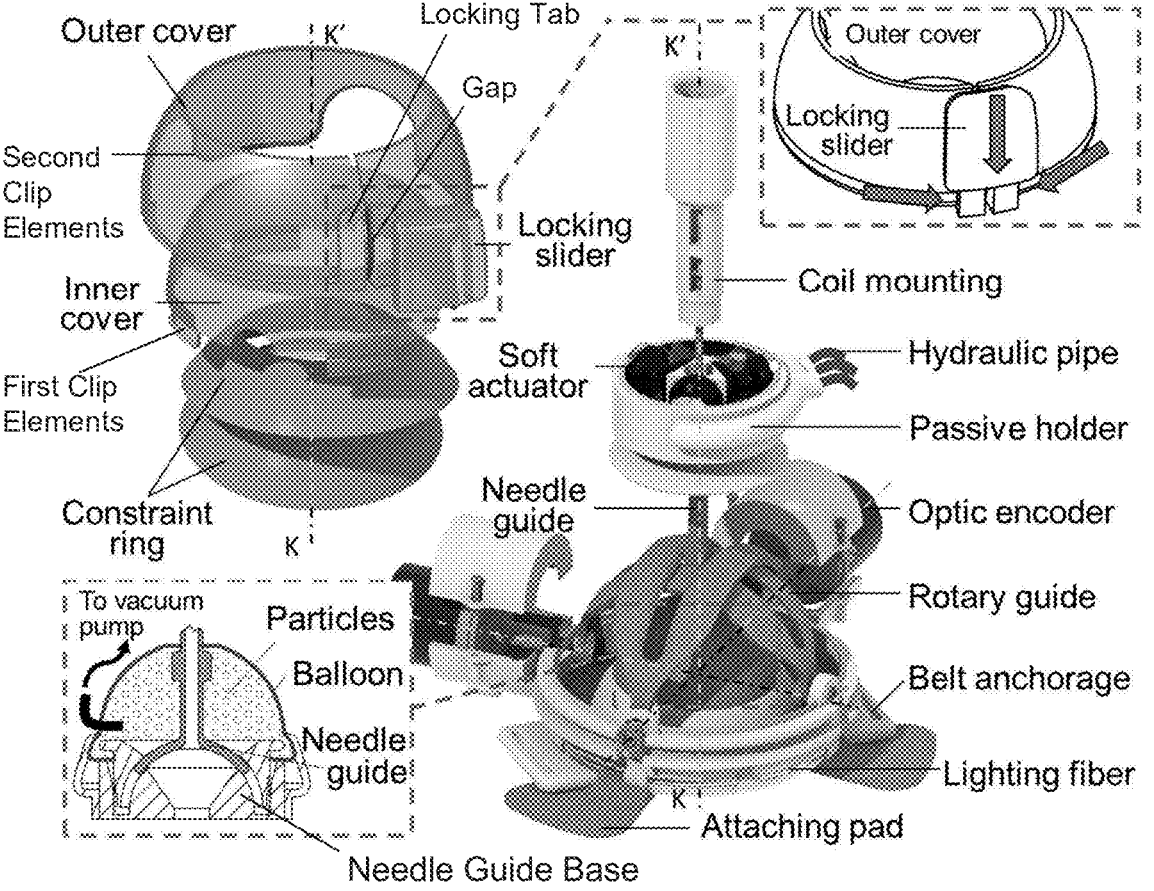

FIG. 3 depicts an exploded view of the robot interior structure. A locking slider is used to manually fix the passive holder orientation. A small pack of particles encloses the needle guide, ensuring rigid fixture for needle insertion.

Figure 4:
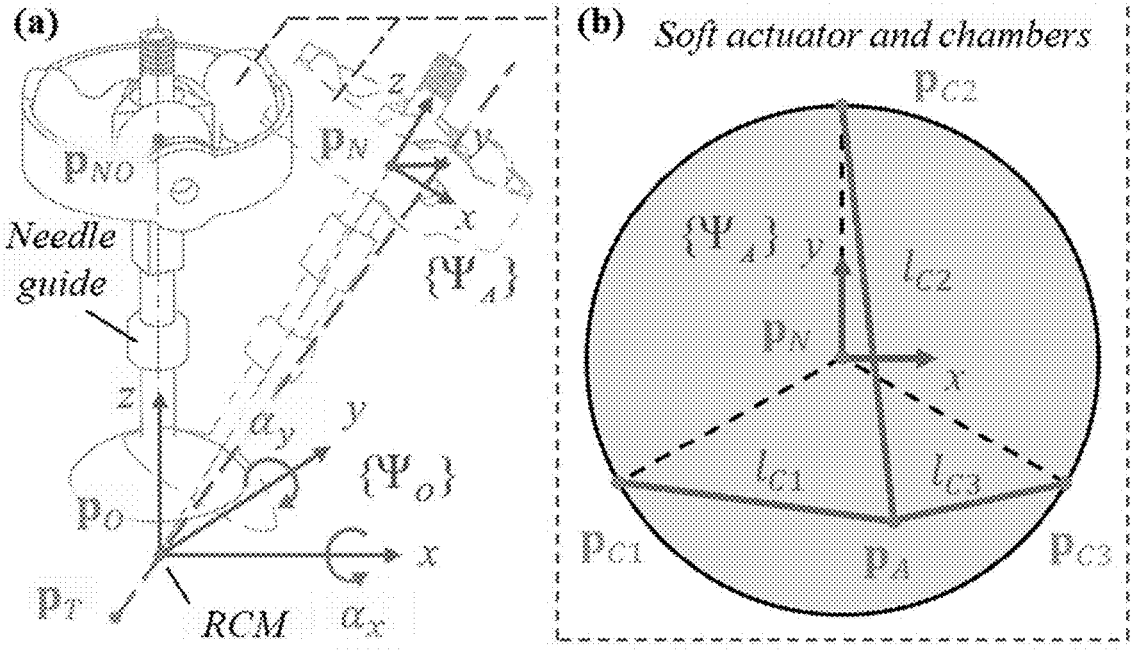

FIG. 4(a) depicts a schematic diagram showing the DoFs of the needle guide. Its initial (vertical) and inclined pose are both constrained by the RCM at the incision point. Angles $\alpha_x$ and $\alpha_y$ about the X- and Y-axis of the frame $\{\psi_o\}$, respectively, denote the needle guide orientation. FIG. 4(b) depicts a schematic of the soft actuator with the length of $i^{th}$ fluidic chamber denoted by $l_{ci}$.

Figure 5:
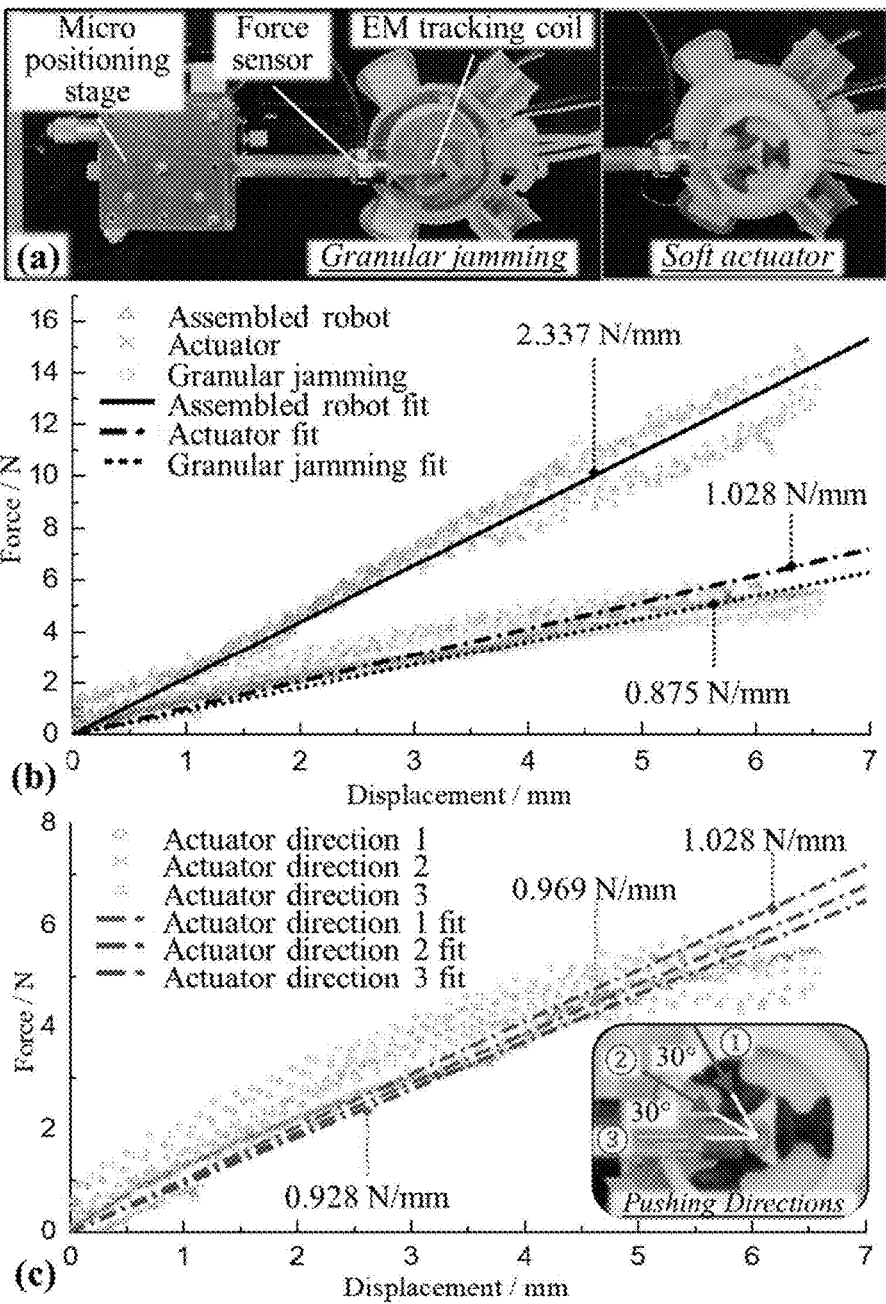

FIG. 5(a) reports experimental setup for stiffness tests; FIG. 5(b) graphically illustrates the relationship between force and displacement showing the transmission stiffness of the granular jamming, soft actuator, and the assembled robot; and FIG. 5(c) graphically illustrates the transmission stiffness of the soft actuator in the three directions. Three pushing directions (arrow) with 30° intervals to evaluate the stiffness of soft actuator.

Figure 6:
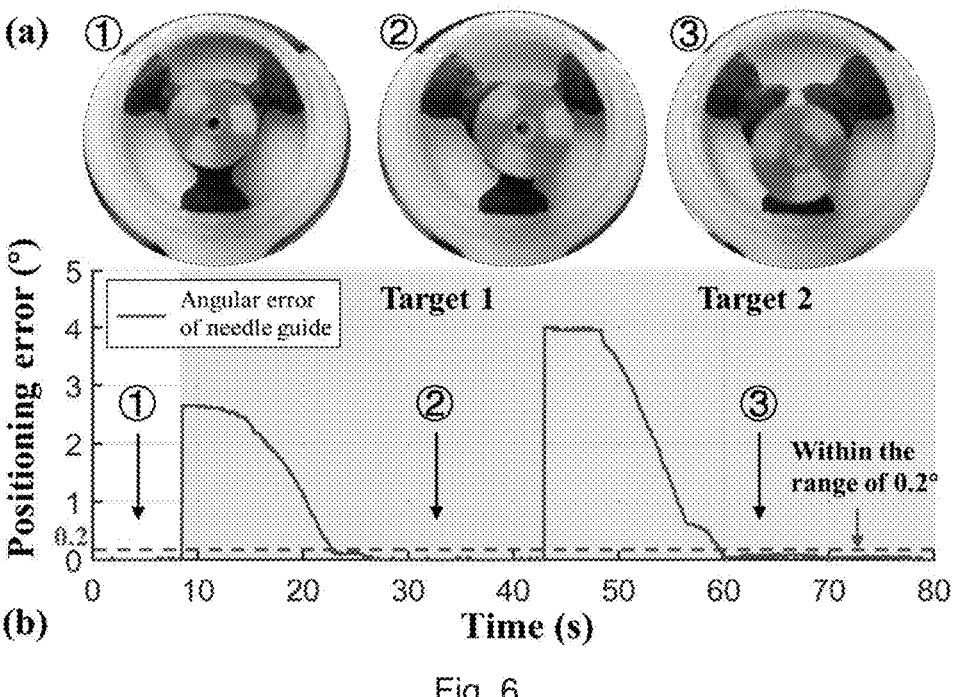

FIG. 6(a) Top view of the soft actuator and the needle guide showing the positions at the three stages; and FIG. 6(b) graphically illustrates the Angular positional error between the desired and actual orientations under feedback control.

Figure 7:
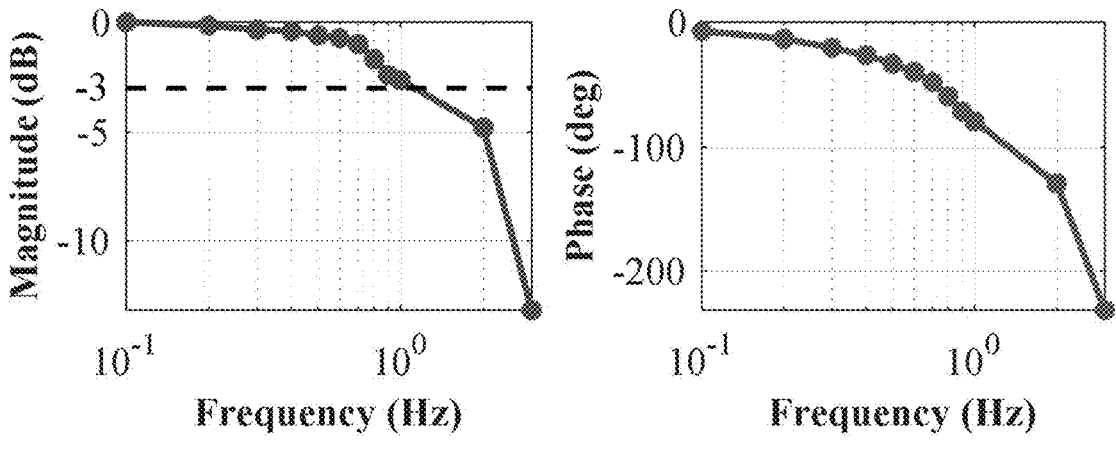

FIG. 7 graphically illustrates the frequency response test of the soft hydraulic actuator. The input is positional signal of electric motor, and the output is displacement of the soft actuator. The bandwidth of the actuator is 1.1 Hz at the cut-off frequency.

Figure 8:
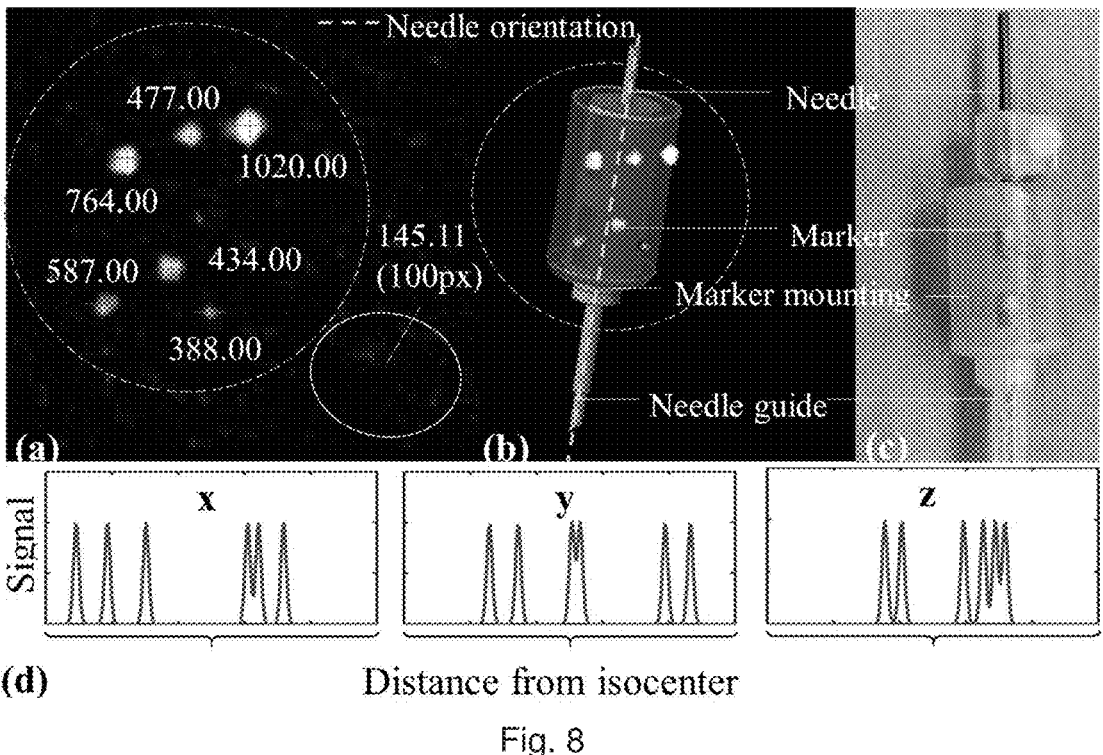

FIG. 8(a) depicts six wireless RF markers revealed under MRI. Labeled signal intensities are measured at the red crosses; FIG. 8(b) depicts a virtual configuration of the needle guide augmented on the markers; FIG. 8(c) depicts actual prototype of needle guide integrated with the six RF markers; and FIG. 8(d) depicts six RF signal peaks in 1-D projections tracking along the orthogonal axes.

Figure 9:
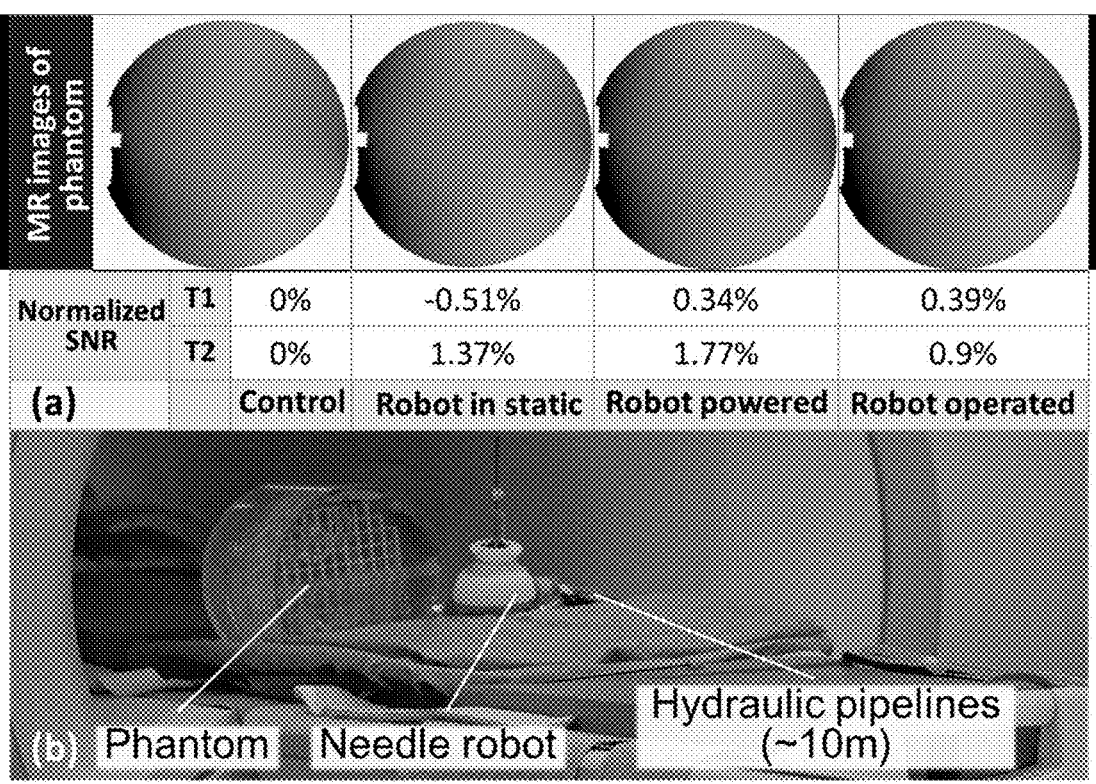

FIG. 9(a) depicts MR images of an MRI phantom put beside the robot showing the negligible EM interference in four operating conditions. The normalized SNR results are summarized in the table. FIG. 9(b) depicts experimental setup of the robot in the 1.5T MRI scanner.

DETAILED DESCRIPTION

The proposed workflow can be divided into four stages, namely preparation, planning, targeting, and intervention, which are shown in FIG. 2a. It is estimated to take 3 hours in total, with approximate time cost for each stage listed as: 1) Preparation in 20 minutes; 2) Planning in 72 minutes (26 minutes for each MR scan [26]); 3) Targeting in 56 minutes; 4) Intervention in 30 minutes [27]. The total procedure time is comparable to the MRI-guided radiofrequency ablation for hepatic malignancies, which takes 2-5 hours in general [8]. To treat multiple tumors, the proposed compact and lightweight robot design can offer a more efficient option using several robots simultaneously for targeting and intervention. Detailed descriptions of each stage are listed below:

Stage 1: Preparation

According to pre-operative MRI images from early observation and diagnosis, a rough estimation of the target position should be found for the treatment or biopsy. The patient is also positioned on the MRI table in this stage.

Stage 2: Planning

The patient undergoes pre-interventional imaging to obtain a high-resolution 3D dataset of the region of interest. The needle insertion path, incision port and hence the robot position is determined by the surgeon based on this image set. The robot is then attached to the patient body accordingly by adhesive pads and a fastening belt. Robot registration is then performed with a second round of MR scans to localize the robot relative to the target.

Stage 3: Targeting

Targeting can be divided into three steps: 1) The orientation of the needle guide is adjusted manually by the surgeon following lighting instructions. When the error between the desired orientation and the actual orientation is greater than 20°, between 5° and 20° and less than 5°, the red light, purple light and the green light will be turned on respectively, which as shown in FIG. 2b. This step is so called coarse adjustment of the robot. 2) Manual locking will be applied by operating a switch on the outer shell of the robot. 3) The patient will be moved to the MRI bore for automatic needle guide positioning, which is fine adjustment, under real-time MR tracking. Afterwards, the needle guide is further locked by the granular jamming module inside the robot.

Stage 4: Interventional Procedures

The patient is moved out of the MRI bore for manual insertion of the needle by the surgeon. The allowable insertion depth is preset by a measured needle stop. The patient is then moved into the MRI bore for treatment/biopsy. Intra-op imaging can be performed based on the surgical requirement, e.g. heat diffusion monitoring for RF ablation of HCC.

Methodology

This section provides the mechanical design and kinematics model of our proposed robotic platform. The device is designed to assist the surgeon in performing intra-op MRI-guided percutaneous needle interventions, such as radiofrequency and laser ablation for the abdominal organs (e.g. liver and kidney).

Robot Design Criteria

For the robotic device, the design and clinical considerations are summarized as follows:

(1) Dexterity. The necessary DoFs to achieve an RCM for single port intervention include needle pan and tilt adjustment. The structure of the manipulator should also allow ample insertion angle (−32° to 24° about normal from the patient's skin [20]) for flexible needle trajectories, particularly for larger tumors (>Ø3 cm) that require ablation at multiple sites.

(2) Size and weight. The main body of the robot should be compact enough to enable flexible mounting on the patient body inside the MRI bore. The robot footprint should be smaller than the standard imaging loop coil (Part No. 10185554, Siemens Medical Solutions, USA) with Ø110 mm diameter. Furthermore, multiple fixtures with robots should be considered for the need of multiple incisions in some cases. The robot should be lightweight to allow easy handling by the surgeon as well as minimizing the burden on the patient.

(3) Positioning accuracy. In the case of liver interventions, the positioning accuracy of the probe tip should be less than 3 mm [28] according to the minimum size of tumor suitable for RF ablation.

(4) MR-safety. The system must be constructed from materials that fulfil the MRI compatibility standard set by ASTM F2503-13 [29]. This restricts material selection to those that are not conductive, metallic or magnetic. Also, the robot operation should not cause electromagnetic (EM) interference that may deteriorate MR imaging or instrument tracking.

Overview of the Robotic Platform

The proposed robotic platform is designed to be mounted directly on the patient or on a loop coil in order to mitigate the effects of patient movement. Three attaching pads with adhesive and a fasten belt are used as anchorage (FIG. 3).

The robot is compact (Ø108 mm×115 mm height) and lightweight (189 g), enabling flexible setup inside the confined MRI bore. The needle guide of the robot can be manipulated in 2 DoFs, including pitch and yaw around an RCM at the insertion point predetermined by the surgeon. The system provides semi-automated needle positioning with the core features: i) automatic needle orientation adjustment in a small motion range by a soft fluid-driven actuator; ii) passive needle holder manually operated by the surgeon for coarse orientation adjustment within a large (±30°) range; iii) granular jamming incorporated to ensure rigid fixture for needle insertion. This semi-automated actuation design with locking system can reduce the actuator requirements of motion range and output force, while keeping the precision of needle targeting. Compared to the fully automatic design that usually requires a larger size of robot (>200 mm length x 200 mm width [22, 23]), the small size of our robot enables more flexibility and convenience in practice. This allows simultaneous setup of multiple robots on the body of the patient for needle targeting, which can shorten the operation time and scanning procedures for the scenarios requiring multiple needle insertion.

To minimize interference with MR imaging, the main structure of the robot is 3D-printed with biocompatible polymers (MED610, Stratasys Inc., USA). The remaining components are also made of non-conductive, non-metallic and non-ferromagnetic materials.

Soft Fluid-driven Actuator

The proposed robot incorporates a soft fluid-driven actuator [30] (Ø40 mm×10 mm height) for the fine adjustment of the needle guide. The fluidic chambers in the soft actuator is 3D-printed with polymers (Agilus 30, Stratasys Inc., USA). 2-DoF planar motion can be generated by the three soft chambers (FIG. 3), which are filled with distilled water. The chambers are connected through 10 m long pipelines to the master cylinders, which are actuated by electric motors. This hydraulic actuation approach [31, 32] features low transmission latency (160 ms on average under 1.1 Hz) and high stiffness (2.337 N/mm), which are validated by the experiments in the sections Transmission Stiffness and Positional Frequency Response. To achieve accurate and responsive transmission as well as flexible setup, the hydraulic pipelines are chosen as semi-rigid nylon (polycaprolactam 6) with inner diameter of 2 mm, referring to the results of previous study [31]. The soft actuator is connected to the needle guide, which can be manipulated within a range of ±5° in two directions for the fine adjustment. Although sacrificing the ability of full-range automated positioning, the actuator can retain small size with lower requirements for motion range and output force, which could also ensure safety by minimizing the potential damage to the patient upon any undue mechanical failure.

To obtain the angular position of the needle guide, two MR safe optical absolute rotary encoders (ZapFREE® MR431, Micronor Inc., Camarillo, USA) with a resolution of 0.044° are incorporated. The positional information is also used for feedback control of the soft actuator with a PID controller. Its performance is evaluated experimentally in the section Feedback Control of The Fluid-Driven Actuator.

Passive Needle Holder During coarse adjustment of the needle guide, the surgeon will grip the robot by the passive holder as labeled in FIG. 3. The passive holder is nested between the outer and inner cover which works with the constraint ring to both constrain its axial motion and act as a friction-lock for the coarse adjustment once the locking slider is pushed into place. The desired needle guide orientation and corresponding optical encoder angles are calculated based on the target selected from preliminary MR imaging Fiber-optic lighting transmits light signals to the surgeon to indicate that the needle guide orientation is within ±5° of the desired orientation (the maximum angle achievable by fine adjustment) and that manual locking can be performed. Note that the outer cover, inner cover, and passive holder are concentric and move along a spherical surface, ensuring an RCM throughout the positioning procedures.

Granular Jamming Locking of Needle Guide

Alongside manual locking of the passive needle holder, granular jamming is integrated into the robot design to provide a second level of locking once fine adjustment with the soft actuator is complete. A small pack of granules sealed in an elastic cover encloses the needle guide, allowing stiffness modulation when a vacuum is induced. The granules are 2 mm diameter PVC spheres that have sufficient smoothness so as to not greatly hinder the needle guide movement when at rest.

Targeting Kinematics

The schematic diagram of the robot is depicted in the FIG. 4a-b. A coordinate frame $\{\psi_p\}$, is defined at the RCM point $p_0$, about which the needle guide can revolve. When the actuator is at rest, the actuation block is at the center point $p_N$, and the needle guide is perpendicular to the plane of the soft actuator. A coordinate frame $\{\psi_A\}$ is defined at the point $p_N$ and moves with the actuator.

The initial pose of the needle guide is along the Z-axis of the frame $\{\psi_o\}$. After the coarse adjustment of the robot, the angular positions of the needle guide with respect to (w.r.t.) the coordinates X and Y of $\{\psi_o\}$ can be denoted as $\alpha_x$ and $\alpha_y$, respectively. The rotation matrix of the coordinate frame $\{\omega_A\}$ w.r.t. $\{\psi_o\}$ can be described with ZYX Euler angles:

$$R(\phi)=R_z(\phi){\cdot}R_y(\theta){\cdot}R_x(\gamma), \quad (1)$$

where the angles $\phi=[\varphi\ \theta\ \gamma]^T$ represent rotations defined w.r.t. the frame $\{\psi_0\}$ along the Z-, Y- and X-axis respectively. The values of each angle can be found as $\varphi=0$, $\theta=\alpha_x$, and $\gamma$ can be derived based on $\alpha_y$ according to the geometric relations. Then the position of $p_N$ can be obtained as:

$$P_N=R(\phi)P_{NO}, \tag{2}$$

where $p_{NO}$ is the center coordinate of the actuator at the initial pose. In the same way, the coordinates of the soft chamber base points $p_{c1}$, $p_{c2}$ and $p_{c3}$ can also be obtained. For an array of inputs from the actuator chambers $q=[I_{C1}, I_{C3}, I_{C4}]T$, the new position of the actuation block $P_A$ can be solved by the equation set:

$$I_{Ci}=\|P_A-P_{ci}\|,i=1,2,3. \tag{3}$$

The motion range of the chambers are $I_{C1}$, $I_{C2}$, $I_{C3}\in$ [5 mm, 15 mm]. The actuation block position $P_A$ is kept within the X-Y plane of the frame $\{\Psi_A\}$ by the constraint:

$$(P_A-P_N)\cdot(P_N-P_o)=0. \tag{4}$$

Then the orientation of the needle guide r can be denoted by:

$$r = \frac{p_O - p_A}{\|p_O - p_A\|}. \tag{5}$$

Given a needle insertion depth $d_i$ defined from the actuation block position $P_A$ to the target, position of the needle tip $P_T$ can be calculated as:

$$P_T=P_A+d_i r \tag{6}$$

To solve the inverse kinematics based on the desired tip position $P_T$, co-registration between image coordinate system and the robot is executed first. The robot is assumed to have been manually adjusted and fixed and the needle guide orientation is within the motion range of the actuator. The desired needle orientation $r_d$ can be expressed as:

$$r_d = \frac{p_T - p_O}{\|p_T - p_O\|}, \tag{7}$$

Then the desired coordinate of actuation block $P_A$ can be obtained by solving the equation set of (4) and (5), with the conditions that $P_A$ is located simultaneously in the direction of $r_d$ and on the X-Y plane of $\{\psi_A\}$. In the end, the desired inputs of each chamber $q=[I_{C1}, I_{C2}, I_{C3}]^T$ can be solved by substituting $p_A$ into (3). The desired encoder angles $\alpha_x$ and $\alpha_y$ can also be calculated based on the needle orientation $r_d$.

Performance Evaluation

Transmission Stiffness

To verify the robot's ability to resist external disturbances, experiments were conducted to test the stiffness of: i) the soft actuator; ii) the locking system using granular jamming; iii) a combination of the soft actuator and granular jamming During the test, the robot frame was fixed at the initial pose and the coarse adjustment part was locked. The soft actuator was connected to the master cylinders, which were actuated by electrical DC motors. 10 m long pipelines filled with distilled water were adopted to connect the slave soft actuator chambers and the master cylinders. For the test i) and iii), the soft actuator chambers were preloaded by the master cylinders with fixed stroke. For the test ii), the soft actuator was detached to ensure no influence on the stiffness of granular jamming During the experiments, a rod is attached on a sliding platform and advanced horizontally to push the needle guide (FIG. 5a). A high precision force sensor (Nano17, ATI Industrial Automation) with 5-Nm sensitivity was used to measure the axial force generated on the rod. The displacement at the contact point was measured by a 6-DoF EM tracking coil (Aurora, NDI Medical, Canada). The advancement of the rod was performed repeatedly for 10 cycles for each test.

FIG. 5b-c illustrate the force-displacement plots of the soft actuator and granular jamming The data was linearly fitted using least-square regression. For the soft actuator alone, the maximum stiffness is 1.028 N/mm with force applied along the direction 1 (FIG. 5c). The overall stiffness of the system can reach 2.337 N/mm by introducing the granular jamming locking, which contributes to 127.3% increase of stiffness compared with the soft actuator alone. Note that the median interaction force between the needle and porcine liver ex vivo is less than 0.6 N with an insertion speed of 5 mm/s [33]. Compared to the stiffness of needle guide with locking, which is 2.337 N/mm, such interaction force can only cause less than 1 mm displacement to the needle tip. It demonstrates the fluid-driven soft actuator with the granular jamming locking system can provide sufficient stiffness to maintain the pose of needle while interacting with tissue.

Feedback Control of The Fluid-Driven Actuator

A manipulation task was conducted to evaluate the feedback control performance of the soft fluid-driven actuator (FIG. 6a). The coarse adjustment was locked, such that the needle guide can only be manipulated by the soft actuator. The position of the actuation block and the angular position of the needle guide can be converted to each other according to the kinematics in the section Passive Needle Holder. The two absolute MR safe optical encoders were used to record the angular positions of the needle guide along two perpendicular axes for feedback control. A simple PID controller was implemented to control the orientation of the needle guide within the motion range of actuator. FIG. 6b shows the angular positional error between the target and current poses during the task. The needle guide can finally be manipulated and kept around the target orientation steadily with an error less than 0.2°, which also demonstrates the capability of precise actuation by the soft actuator.

Needle Targeting Accuracy

A needle targeting task was carried out to validate the manipulation accuracy of the robotic system. The robot was fixed on a plastic board and placed above the plane containing target points. The separation between the two planes is around 100 mm, which is a typical depth of liver tumor beneath skin. Two sets of targets, with 10 points in each set, are located at two circular ranges (Ø20 mm): a) a range right below the RCM point of the robot; and b) a range that the coarse adjustment part needs to be revolved manually by 30° for needle targeting. These targets coordinates were recorded by the same EM tracking system as in section Transmission Stiffness and registered with the coordinate system of the robot. A phantom needle was used for targeting, with a 6-DoF EM tracking sensor attached at the needle tip to acquire the position.

During the experiment, the orientation of the needle guide was controlled towards the desired orientation. Once pointing to the target, the needle was manually advanced through the needle guide. Then the tip position was measured when the robot was at rest. Such targeting trial was repeated 5 times for each point. The mean error alongside its standard deviation of the measurements was evaluated and summarized in Table I, including the distance from the target to the needle tip and the target to the needle axis. The accuracy is within 0.9 mm and its variation is less than 0.35 mm, demonstrating the accurate needle targeting performance conducted by the fine adjustment of the soft actuator.

Positional Frequency Response

The dynamic performance of the soft actuator with hydraulic transmission was evaluated with a frequency response test. During the experiment, the soft actuator without external loading was set to follow a periodic sinusoidal input from the DC motor through m hydraulic pipelines under open-loop control. It corresponds to a repeated linear

TABLE I

RESULT OF TARGETING ACCURACY TEST

| Needle pose | Needle tip | | Normal to the needle | |
|---|---|---|---|---|
| | Vertical | 30° tilt | Vertical | 30° tilt |
| Accuracy (mm) | 0.89 ± 0.31 | 0.85 ± 0.31 | 0.78 ± 0.28 | 0.67 ± 0.35 | motion with an amplitude of 5 mm and frequency from 0.1 Hz to 3 Hz at the soft actuator side. The positional output of the soft actuator was captured by an EM tracking coil for the bode plot. The experimental result is shown in FIG. 7. The bandwidth of the actuator is 1.1 Hz, which is the cut-off frequency of −3 dB magnitude. The phase lag is kept less than 50° within the bandwidth. The transmission latency, or time delay from the input to output, is measured as 160 ms on average with the frequency less than 1.1 Hz.

MR-Based Tracking Test

MR-based wireless tracking [34] is utilized for measurement of the needle pose under MRI scans. The proposed wireless and miniaturized marker (FIG. 8b-c) integrates circuits specialized for amplifying the MR signal. Therefore, high signal to noise ratio is maintained even with low flip angles)(−1°, which allows localization of markers against anatomical backgrounds as shown in FIG. 8a. Wireless marker positions can be measured using the tracking pulse-sequence [35], enabling real-time acquisition up to 30 Hz [34]. The markers signal can be excited with a non-selective RF-pulse (alpha=1), and then projected along three orthogonal axes respectively with corresponding gradient echo readouts. Spoiler gradients can be also included to dephase the magnetization from the background object. Furthermore, with the use of RTHawk (HeartVista, Inc.) [34], the scanning raw data can be streamed out with low latency (<10 ms), thus offering real-time positional feedback for closed-loop robotics control. As shown in FIG. 8d, the peaks of markers can also be localized along each axis. The true marker positions can be solved by imposing geometry constraints, e.g. distances between each marker pairs, on the possible combination of 1D maker coordinates.

MR Compatibility Test

The MRI-compatibility test was conducted to evaluate the EM interference of the robot to the MR images. During the test, the slave part of the robot was operated inside a 1.5 T MRI scanner (SIGNA, General Electric Company, USA) and was placed near a commercial MRI phantom (J8931, J. M. Specialty Parts, USA) at the isocenter of the scanner (FIG. 9b). The T1-weighted fast field echo (FFE) and T2-weighted turbo spin echo (TSE) sequences were adopted to obtain the MR images. FIG. 9a shows the resultant MR images of the phantom by T2-weighted TSE under four different conditions: i) Control: only phantom placed in the scanner; ii) Static: robot involved and remained power OFF; iii) Powered: robot kept still, but with the hydraulic and electric power ON; iv) In motion: robot in operation. No observable image artifact was found in the MR images under different robot operation scenarios. The control condition served as the baseline for evaluation. The lower part of FIG. 9a also illustrates the results of SNR analysis under the two imaging sequences. The maximum SNR loss in the successive conditions was found within 2% only, even with the robot in full motion.

Disclosed herein are the design, fabrication, and experimental validation of an MRI-guided robot for percutaneous needle procedures. The system provides semi-automated needle positioning, thus interactively guiding the surgeon to adjust the needle towards the target lesions, followed by automatic fine adjustment through closed-loop control of the soft robotic actuator. The compact and lightweight design allows not only the direct mounting of the robot to the body of the patient, but also simultaneous needle targeting at multiple locations with several robots alongside the loop coils. Granular jamming was also implemented to lock the needle position in place once after the fine automated adjustments have been made. The combined stiffness of the granular jamming and soft actuator was experimentally found to reach 2.337 N/mm A needle insertion test was conducted, in which a targeting accuracy <0.9 mm can be achieved. Note that the positioning accuracy test undertaken in this study is only indicative of the needle guide targeting itself, without involving factors such as needle-tissue interaction force, patient movement, or MRI-related effects including inherent image distortion and resolution limitations. In our MRI-compatibility test, only negligible levels of EM interference were observed even while the robot was fully operated with granular jamming actuation and encoding. Apart from the actuator encoding, we have also investigated the use of MR-based wireless tracking markers that can feedback the needle guide pose in real-time in MR image coordinates.

The successful integration of MRI-guided, robot-assisted percutaneous ablation presents a timely improvement over current first-line treatments for HCC. With the possibility for integrating real-time MR-based needle tracking and temperature feedback from intra-op MR thermometry, several key points can be addressed: i) enhanced ablation management of tumors located close to vessels and organs such that thermal damage is confined to the complete safety margins; ii) improved ablation probe access to occluded lesions, minimizing the need for invasive open surgical approaches that may prolong post-operative recovery; iii) reduced recurrence rate of HCC by providing complete tumor ablation, thus reducing complications related to repeat procedures.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

Notes, all of which are Incorporated Herein by Reference:

[8] A. H. Mahnken et al., "MR-guided radiofrequency ablation of hepatic malignancies at 1.5 T: initial results," *Journal of Magnetic Resonance Imaging: An Official Journal of the International Society for Magnetic Resonance in Medicine*, vol. 19, no. 3, pp. 342-348, 2004.

[20] N. Hungr, I. Bricault, P. Cinquin, and C. Fouard, "Design and validation of a CT—and MRI-guided robot for percutaneous needle procedures," *IEEE transactions on robotics*, vol. 32, no. 4, pp. 973-987, 2016.

[22] R. Monfaredi et al., "Development of a shoulder-mounted robot for MRI-guided needle placement: phantom study," *International journal of computer assisted radiology and surgery*, vol. 13, no. 11, pp. 1829-1841, 2018.

[23] G. Li et al., "Body-mounted robotic assistant for MRI-guided low back pain injection," *International Journal of Computer Assisted Radiology and Surgery*, pp. 1-11, 2019.

[26] V. Granata et al., "Surveillance of HCC Patients after Liver RFA: Role of MRI with Hepatospecific Contrast versus Three-Phase CT Scan—Experience of High Volume Oncologic Institute," *Gastroenterology research and practice*, vol. 2013, 2013.

[27] M. W. Lee et al., "Percutaneous Radiofrequency Ablation of Small (1-2 cm) Hepatocellular Carcinomas Inconspicuous on B-Mode Ultrasonographic Imaging: Usefulness of Combined Fusion Imaging with MRI and Contrast-Enhanced Ultrasonography," Canadian *Journal of Gastroenterology and Hepatology*, vol. 2018, 2018.

[28] S.-E. Song, J. Tokuda, K. Tuncali, A. Yamada, M. Torabi, and N. Hata, "Design evaluation of a double ring RCM mechanism for robotic needle guidance in MRI-guided liver interventions," in 2013 IEEE/RST *International Conference on Intelligent Robots and Systems*, 2013: IEEE, pp. 4078-4083.

[29] ASTM F2503-13: *Standard Practice for Marking Medical Devices and Other Items for Safety in the Magnetic Resonance Environment*, ASTM.

[30] L. H. Blumenschein and Y. Mengüc, "Generalized Delta Mechanisms from Soft Actuators," in 2019 2nd *IEEE International Conference on Soft Robotics (RoboSoft)*, 2019: IEEE, pp. 249-256.

[31] Z. Dong et al.,"High-Performance Continuous Hydraulic Motor for MR Safe Robotic Teleoperation," vol. 4, no. 2, pp. 1964-1971, 2019.

[32] Z. Guo et al., "*Compact design of a hydraulic driving robot for intraoperative MRI-guided bilateral stereotactic neurosurgery*," vol. 3, no. 3, pp. 2515-2522, 2018.

[33] D. J. van Gerwen, J. Dankelman, and J. J. van den Dobbelsteen, "Needle—tissue interaction forces—A survey of experimental data," *Medical engineering & physics*, vol. 34, no. 6, pp. 665-680, 2012.

[34] M. A. Rube, A. B. Holbrook, B. F. Cox, J. G. Houston, and A. Melzer, "Wireless MR tracking of interventional devices using phase-field dithering and projection reconstruction," *Magnetic resonance imaging, vol.* 32, no. 6, pp. 693-701, 2014.

[35] M. B. Ooi, S. Krueger, W. J. Thomas, S. V. Swaminathan, and T. R. Brown, "Prospective real-time correction for arbitrary head motion using active markers," *Magnetic Resonance in Medicine: An Official Journal of the International Society for Magnetic Resonance in Medicine, vol.* 62, no. 4, pp. 943-954, 2009.

[36] P. Kulkarni, S. Sikander, P. Biswas, S. Frawley, and S.-E. Song, "Review of Robotic Needle Guide Systems for Percutaneous Intervention," Annals of biomedical engineering, vol. 47, no. 12, pp. 2489-2513, 2019.

[37] Y. Kobayashi, J. Hong, R. Hamano, K. Okada, M. G. Fujie, and M. Hashizume, "Development of a needle insertion manipulator for central venous catheterization," The International Journal of Medical Robotics and Computer Assisted Surgery, vol. 8, no. 1, pp. 34-44, 2012.

[38] Y. Kobayashi et al., "Development of an integrated needle insertion system with image guidance and deformation simulation," *Computerized Medical Imaging and Graphics*, vol. 34, no. 1, pp. 9-18, 2010.

[39] C. J. Walsh, N. C. Hanumara, A. H. Slocum, J.-A. Shepard, and R. Gupta, "A patient-mounted, telerobotic tool for CT-guided percutaneous interventions," *Journal of Medical Devices*, vol. 2, no. 1, p. 011007, 2008

What is claimed is:

1. A method of performing a medical procedure, comprising:

medical imaging to obtain a dataset of a region of interest;

identifying a target position on or within a patient and positioning a patient on an operating table;

identifying the target position relative to the robot position;

determining a needle insertion path, an incision port and robot position based on the data set and the target position;

non-invasive mounting of the robot on the patient at the determined incision port and robot position;

coarse adjustment of the robot performed manually by a surgeon with visual feedback provided by the robot to indicate adjustment accuracy in-situ;

fine adjustment of the robot after coarse adjustment for automatic needle guide positioning guided by one or both of intra-operative medical imaging or robot encoding;

coarse locking of the needle guide after the coarse adjustment, wherein the coarse locking comprises use of an outer cover, wherein the outer cover partially encloses a granular jamming mechanism comprising an elastic membrane having granules enclosed therewithin, and wherein the elastic membrane encloses the needle guide, and wherein the outer cover comprises an expandable ring that is fixed in place around the needle guide, and wherein the fixing comprises installing a locking slider over a locking tab of the outer cover, thereby fixing the outer cover in a fixed shape around the needle guide;

fine locking of the needle guide, after the fine adjustment, by actuating the granular jamming mechanism that provides granular jamming of the needle guide, thereby further limiting movement of the needle guide; and performing the medical procedure on the region of interest.

2. The method according to claim 1, wherein the medical imaging is at least one of computed tomography (CT), X-ray, ultrasound (US), or magnetic resonance imaging (MRI), and wherein the region of interest is in the human body, including the liver, kidney, lung, breast, head, neck, or shoulder.

3. The method according to claim 1, wherein the medical procedure is at least one of biopsy, drug administration, tumor ablation, tissue repair, drainage, or electrode implantation.

4. The method according to claim 1, further comprising:
determining a plurality of robots, a plurality of needle insertion paths, and a plurality of incision ports.

5. The method according to claim 1, wherein the region of interest is a liver within the patient and the medical procedure is treating liver cancer.

6. A patient-mounted robotic device for image-guided percutaneous procedures, comprising:
a needle guide;
a coarse adjustment mechanism that is manually operated by the surgeon to perform coarse adjustment;
a fine adjustment mechanism that is automatically operated under intra-operative real-time imaging guidance and/or robot encoding to perform fine adjustment;
a fiber-optic light that is configured to provide visual feedback to the surgeon during manual operation to indicate targeting accuracy,
wherein the needle guide accommodates a needle-like surgical instrument,
wherein the needle guide pose is measured with encoders and imaging fiducial markers, and
wherein the fine adjustment mechanism comprises:
multiple co-planar fluid-driven soft actuator chambers that act in concert to adjust the needle guide pose;
a master actuation console that provides hydraulic transmission to the soft chambers,
wherein both the coarse adjustment mechanism and the fine adjustment mechanisms pivot the needle guide about a remote center of motion,
wherein the needle guide is lockable through a granular jamming mechanism that limits movement of the needle guide,
wherein the granular jamming mechanism is coarsely jammable by latching an outer cover that partially encloses the granular jamming mechanism, and
wherein the outer cover comprises a ring having an expandable central opening, wherein the latching comprises installing a locking slider over locking tabs of the outer cover, thereby reducing a size of the central opening, and
a base component that allows mounting of the robotic device on the patient using noninvasive attachment to the patient.

7. The patient-mounted robotic device according to claim 6,
wherein the medical imaging is at least one of computed tomography (CT), X-ray, ultrasound (US), or magnetic resonance imaging (MRI), and
wherein the encoders and imaging fiducial markers are compatible with at least one of computed tomography (CT), X-ray, ultrasound (US), or magnetic resonance imaging (MRI).

8. The patient-mounted robotic device according to claim 6, wherein the imaging modality is MRI, the encoders are MRI-compatible, the imaging fiducial markers are MRI-based, and the master actuation console is located outside of the operating (MRI) room.

9. The patient-mounted robotic device according to claim 6, wherein the imaging modality is CT, X-ray, or ultrasound (US), the encoders are CT-, X-ray-, or US-compatible, and the imaging fiducial markers are CT- X-ray-, or US-based.

10. The patient-mounted robotic device according to claim 6, having a weight of 0.5 kg or less, wherein the patient-mounted robotic device is mountable on the patient's abdomen.

11. The patient-mounted robotic device according to claim 6, fit within a standard loop coil for MRI imaging.

12. The patient-mounted robotic device according to claim 6, wherein two or more robots, including the robot are simultaneously mounted to the patient for multiple needle insertions.

13. The patient-mounted robotic device according to claim 6, wherein the remote center of motion is located directly at the incision port when the device is mounted to the patient.

14. The patient-mounted robotic device according to claim 6, wherein the granular jamming mechanism comprises an elastic membrane having granules enclosed therewithin, wherein an actuation of the granular jamming mechanism comprises applying vacuum to the granules within the elastic membrane, and wherein the elastic membrane is at least partially enclosed within the outer cover.

15. A method of performing a medical procedure, comprising:
medical imaging to obtain a dataset of a region of interest;
identifying a target position on or within a patient and positioning a patient on an operating table;
identifying the target position relative to the robot position;
determining a needle insertion path, an incision port and robot position based on the data set and the target position;
non-invasive mounting of the robot on the patient at the determined incision port and robot position;
coarse adjustment of the robot performed manually by a surgeon with visual feedback provided by the robot to indicate adjustment accuracy in-situ;
fine adjustment of the robot after coarse adjustment for automatic needle guide positioning guided by one or both of intra-operative medical imaging or robot encoding;
granular jamming of the needle guide, by actuating a granular jamming mechanism, thereby limiting movement of the needle guide;
enclosing of the granular jamming mechanism by latching an outer cover at least partially over the granular jamming mechanism,
wherein the outer cover comprises a non-continuous ring, and wherein the latching comprises installing a locking slider over locking tabs of the outer cover, thereby fixing the position of the locking tabs relative to one another; and
performing the medical procedure on the region of interest.

16. The method of claim 15, wherein the granular jamming mechanism comprises an elastic membrane having granules enclosed therewithin, wherein actuation of the granular jamming mechanism comprises applying vacuum to the granules within the elastic membrane, and wherein the elastic membrane is partially enclosed within the outer cover.

17. The method according to claim 1,
wherein the outer cover further encloses a flexible rotary
guide, and wherein the installing the locking slider over
the locking tab fixes the outer cover in a fixed shape
around the rotary guide, which rotary guide thus con-
strains a passive holder supporting the needle guide,
and thereby also friction-locking the coarse adjustment.

18. The method according to claim 1,
wherein the coarse locking further comprises installing an
inner cover over a needle guide base that fixedly
supports the needle guide, and
wherein the installing the outer cover comprises installing
the outer cover over the inner cover and into fixed
engagement with the inner cover.

19. The method according to claim 18,
wherein the inner cover comprises first clip elements, the
outer cover comprises second clip elements, and the
outer cover is installed over the inner cover in a manner
that fixedly engages the first clip elements and the
second clip elements.

20. The method according to claim 19,
wherein the locking tab comprises a second clip element
of the second clip elements, and
wherein installing of the locking slider over the locking
tab provides a final clipping of the outer cover to the
inner cover.

\* \* \* \* \*